(12) United States Patent
Nelson (10) Patent No.: US 7,309,571 B2
(45) Date of Patent: Dec. 18, 2007

(54) AMPLIFICATION OF SELF-LIGATED, CIRCULARIZED CDNA FOR EXPRESSION PROFILING

(75) Inventor: John Nelson, Hillsborough, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 503 days.

(21) Appl. No.: 10/770,657

(22) Filed: Feb. 3, 2004

(65) Prior Publication Data

US 2004/0180372 A1    Sep. 16, 2004

Related U.S. Application Data

(60) Provisional application No. 60/444,601, filed on Feb. 3, 2003.

(51) Int. Cl.
*C12Q 1/68* (2006.01)
*C12P 19/34* (2006.01)

(52) U.S. Cl. .......................... 435/6; 435/91.2
(58) Field of Classification Search .................. 435/6, 435/91.2
See application file for complete search history.

(56) References Cited

U.S. PATENT DOCUMENTS

| | | | |
|---|---|---|---|
| 5,849,547 A | 12/1998 | Cleuziat et al. | |
| 5,854,033 A * | 12/1998 | Lizardi | 435/91.2 |
| 5,876,932 A * | 3/1999 | Fischer | 435/6 |
| 6,124,120 A * | 9/2000 | Lizardi | 435/91.2 |
| 6,203,984 B1 * | 3/2001 | Hu et al. | 435/6 |
| 6,323,009 B1 | 11/2001 | Lasken et al. | |
| 6,977,153 B2 * | 12/2005 | Kumar et al. | 435/6 |
| 2002/0004592 A1 * | 1/2002 | Connor et al. | 536/24.3 |
| 2002/0164629 A1 * | 11/2002 | Quake et al. | 435/6 |
| 2003/0082559 A1 * | 5/2003 | Beach et al. | 435/6 |
| 2004/0076966 A1 * | 4/2004 | Windsor et al. | 435/6 |

FOREIGN PATENT DOCUMENTS

WO    WO02/057447    7/2002

OTHER PUBLICATIONS

Lizardi, P., "Mutation Detection and Single-Molecule Counting Using Isothermal Rolling-Circle Amplification", Nature Genetics, vol. 19, Jul. 1998, pp. 225-232.

* cited by examiner

*Primary Examiner*—Kenneth R. Horlick
(74) *Attorney, Agent, or Firm*—Yonggang Ji (57) ABSTRACT

This invention presents a new cDNA amplification method. RNA is first converted to cDNA. The synthesis of cDNA can include a promoter tagged oligonucleotide, and then this cDNA is ligated to form circles (or possibly concatemers). This is then amplified using a Phi29 DNA polymerase based rolling circle and strand displacement amplification. The invention allows for RNA promoter sequences to be attached to the cDNA to facilitate additional amplification through the generation of RNA from the amplified cDNA. The resulting product can then be used to make materials for gene expression studies or other RNA analysis procedures.

16 Claims, 7 Drawing Sheets

Comparison of amplified cDNA and direct 1st strand cDNA labeling

FIGURE 6

Quantitative PCR analysis of beta actin cDNA levels in unamplified and amplified cDNA samples

SEQUENCE LISTING

<160> NUMBER OF SEQ ID NOS: 4

<210> SEQ ID NO 1
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 1
gcggccgcgt aatacgactc actatagggt ttttttttt ttttttttt ttt      53

<210> SEQ ID NO 2
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 2
gcgtgatggt gggcat      16

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 3
gatggggtac ttcagggt      18

<210> SEQ ID NO 4
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 4
ggattcctat gtgggcga      18

AMPLIFICATION OF SELF-LIGATED, CIRCULARIZED CDNA FOR EXPRESSION PROFILING

CROSS-REFERENCE TO RELATED APPLICATIONS

This application claims priority to U.S. Provisional Application Ser. No. 60/444,601 filed on Feb. 3, 2003, the entire disclosure of which is incorporated herein.

BACKGROUND OF INVENTION

1. Field of the Invention

The disclosed invention is generally in the field of nucleic acid amplification and expression profiling.

2. Description of Related Art

A number of methods have been developed for exponential amplification of nucleic acids. These include the polymerase chain reaction (PCR), ligase chain reaction (LCR), self-sustained sequence replication (3SR), nucleic acid sequence based amplification (NASBA), strand displacement amplification (SDA), multiple displacement amplification (MDA, U.S. Pat. No. 6,124,120), and rolling circle amplification (RCA, U.S. Pat. No. 6,143,495).

Current methods of PCR amplification involve the use of two primers which hybridize to the regions flanking a nucleic acid sequence of interest such that DNA replication initiated at the primers will replicate the nucleic acid sequence of interest. By separating the replicated strands from the template strand with a denaturation step, another round of replication using the same primers can lead to geometric amplification of the nucleic acid sequence of interest. PCR amplification has the disadvantage that the amplification reaction cannot proceed continuously and must be carried out by subjecting the nucleic acid sample to multiple cycles in a series of reaction conditions.

A variant of PCR amplification, termed whole genome PCR, involves the use of random or partially random primers to amplify the entire genome of an organism in the same PCR reaction. This technique relies on having a sufficient number of primers of random or partially random sequence such that pairs of primers will hybridize throughout the genomic DNA at moderate intervals. Replication initiated at the primers can then result in replicated strands overlapping sites where another primer can hybridize. By subjecting the genomic sample to amplification cycles, the genomic sequences will be amplified. Whole genome PCR has the same disadvantages as other forms of PCR.

A field in which amplification is particularly relevant is RNA expression profiling, where the objective is to determine the relative concentration of many different molecular species of RNA in a biological sample. Some of the RNA's of interest are present in relatively low concentrations, and it is desirable to amplify them prior to analysis. It is not possible to use the polymerase chain reaction to amplify them because the mRNA mixture is complex, typically consisting of 5,000 to 20,000 different molecular species. The polymerase chain reaction has the disadvantage that different molecular species will be amplified at different rates, distorting the relative concentrations of mRNAs.

Some procedures have been described that permit moderate amplification of all RNA's in a sample simultaneously. For example, in Lockhart et al., Nature Biotechnology 14:1675-1680 (1996), double-stranded cDNA was synthesized in such a manner that a strong RNA polymerase promoter was incorporated at the end of each cDNA. This promoter sequence was then used to transcribe the cDNA's, generating approximately 100 to 150 RNA copies for each cDNA molecule. This weak amplification system allowed RNA profiling of biological samples that contained a minimum of 1,000 cells. However, there is a need for a more powerful amplification method that would permit the profiling analysis of samples containing a very small number of cells. Also, a number of methods use an RNA polymerase promoter attached to the 5' end of primer used to generate the first strand during cDNA synthesis. A second strand is then generated and the resultant double stranded cDNA is transcribed to make an antisense RNA transcript which can be used for expression studies. However, the level of amplification is very limited.

Accordingly, there is a need for amplification methods that are more reliable, and produce greater amplification in a shorter time. This concern is addressed in greater detail below.

SUMMARY OF INVENTION

Figure 1:
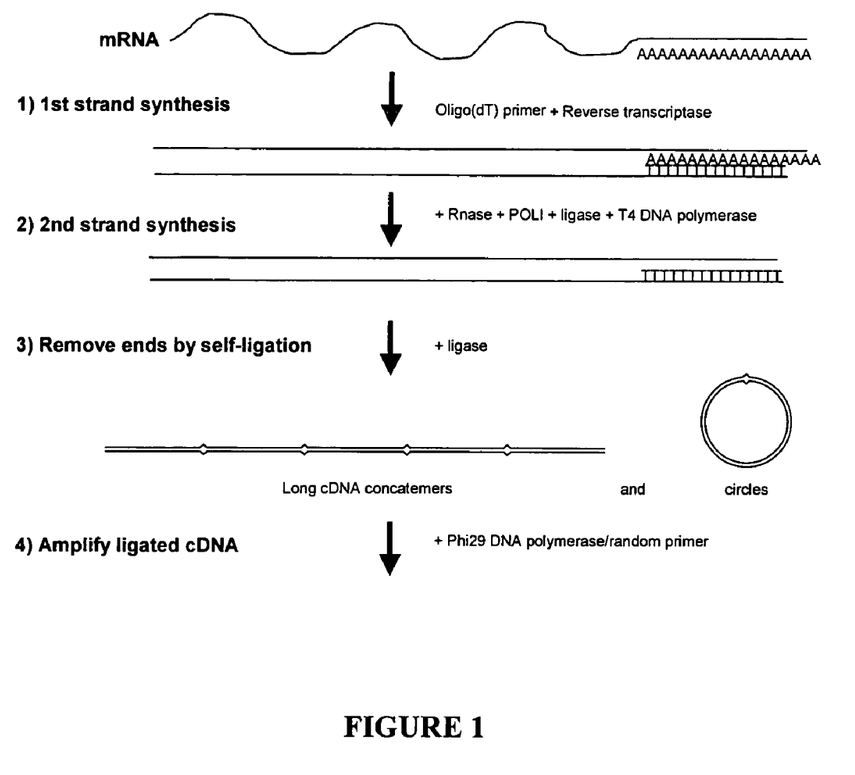
FIG. 1 presents a schematic of the workflow of the amplification methodology.

This invention presents a new cDNA amplification method which allows for greater levels of amplification of RNA sequences. The mRNA is first converted to cDNA. The synthesis of cDNA can include a promoter tagged oligonucleotide, and then this cDNA is blunt-end ligated to form circles (or possibly concatemers). This is then amplified using a Phi29 DNA polymerase based random primed strand displacement amplification method (see FIG. 1) as described in U.S. Pat. No. 6,323,009, incorporated herein by reference. The resulting product can then be used to make materials for gene expression studies.

This method is designed to allow for gene expression analysis from small numbers of cells. The cDNA made from this type of sample will have a very low concentration, which will minimize concatenation; instead, for the most part, the cDNA will circularize. The circularized cDNA serves as the input template for amplification. In practice the cDNA that has been ligated to form circles (monomer size), either with or without concatemers, can be amplified by rolling circle amplification and/or strand displacement amplification. Both of these amplification methods rely on amplification by strand displacement DNA synthesis (ASD) during which double stranded templates are replicated by a strand displacing polymerase resulting in the net gain of polymerized material without temperature cycling to denature the double stranded templates. The methodology permits both random primed and specific primed amplification methods.

Figure 5:
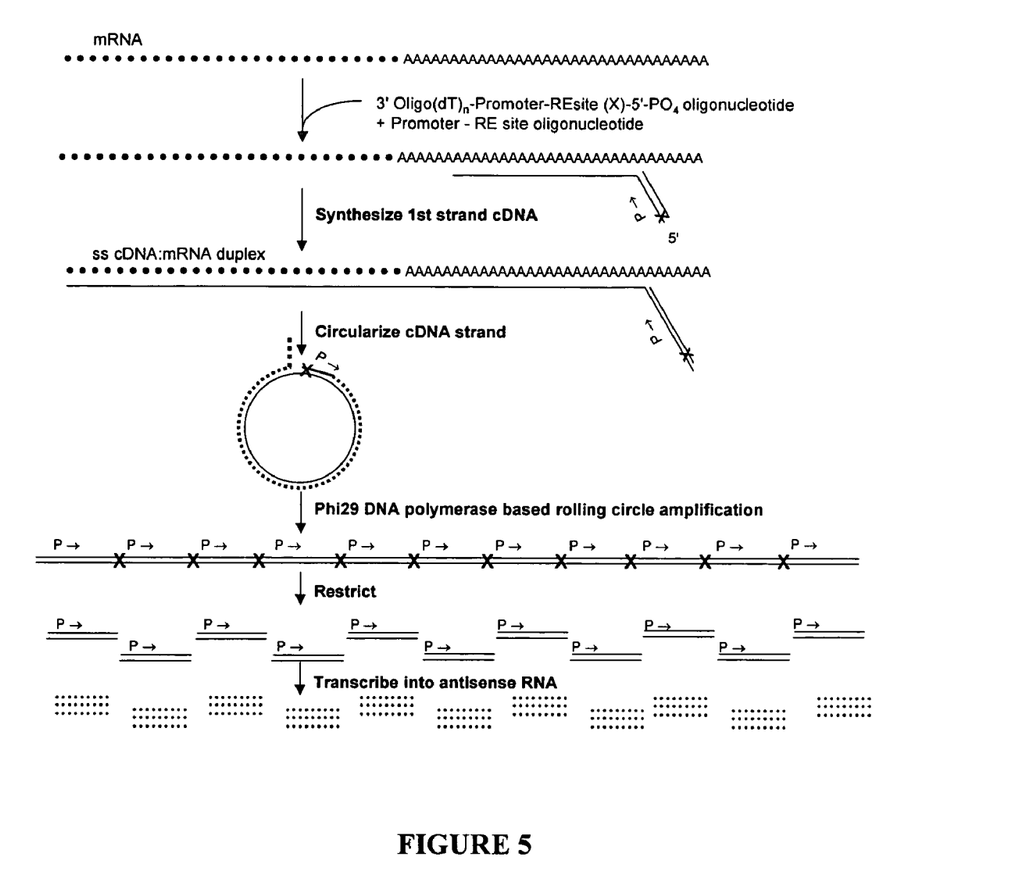
FIG. 5 presents a schematic of the methodology for amplification of first strand cDNA.
Figure 6:
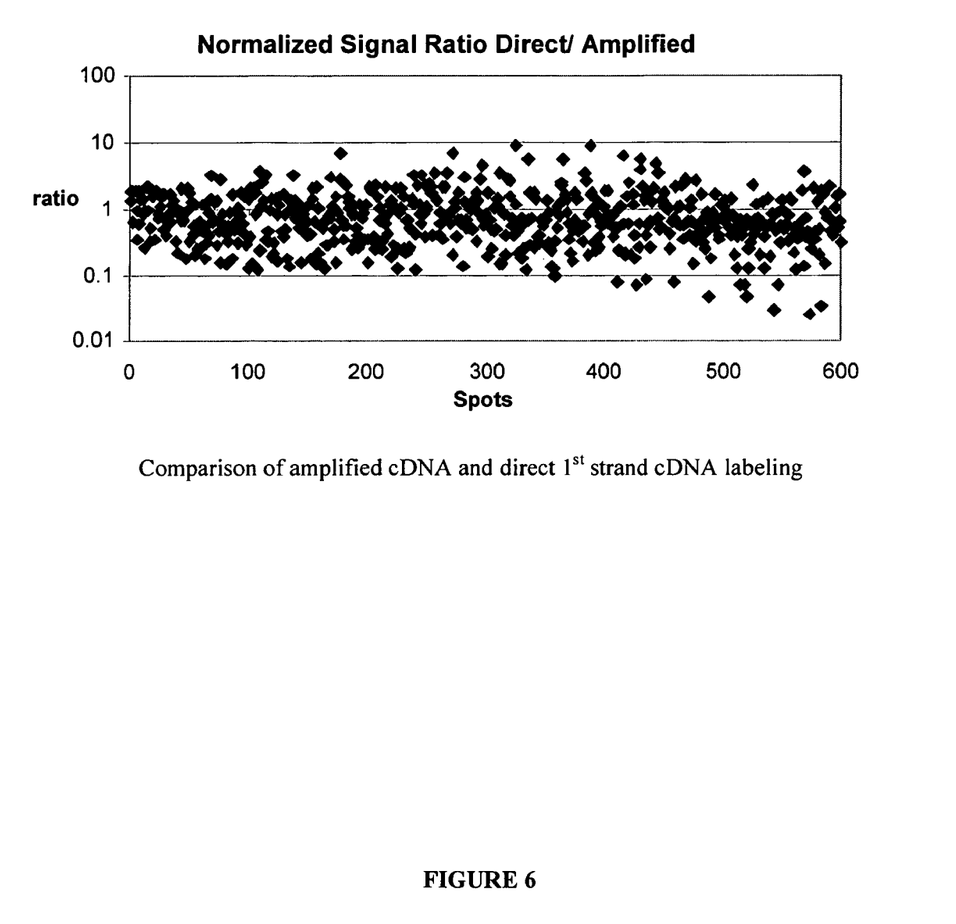
Figure 7:
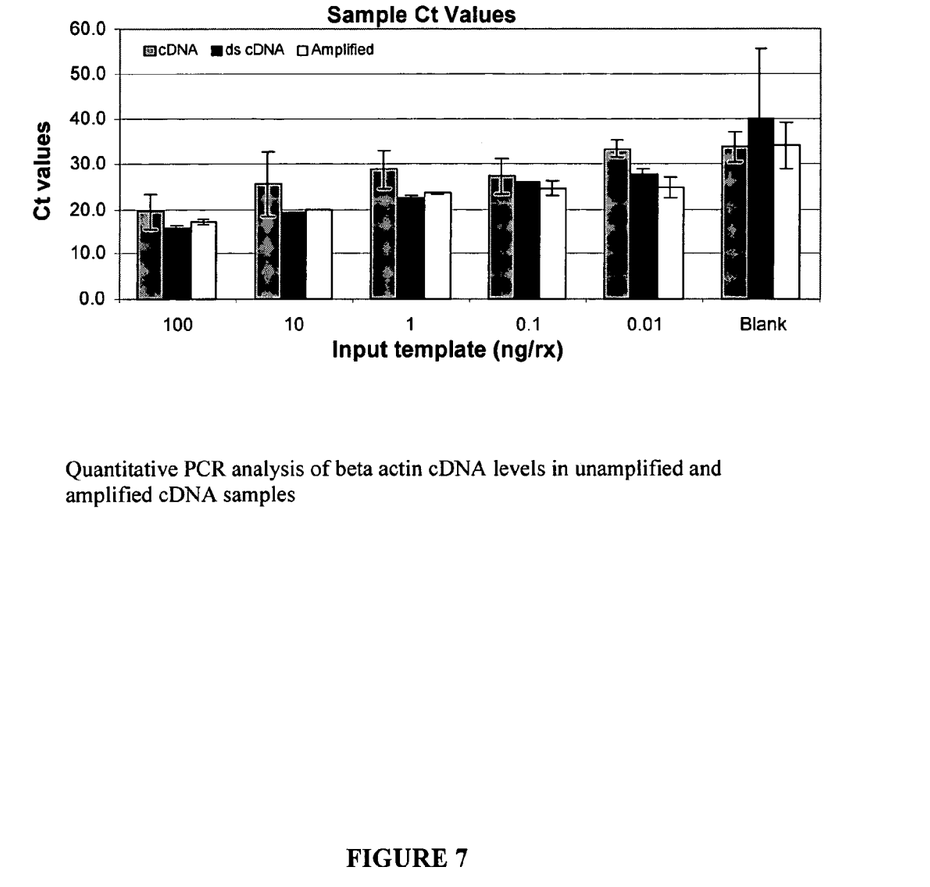
FIG. 7 presents the results of quantitative PCR analysis of beta actin cDNA levels in unamplified and amplified cDNA samples. Beta actin gene specific primers were used to perform real-time quantitative PCR from either $1^{st}$ strand cDNA, double stranded cDNA or double stranded cDNA which has been circularized and then amplified using random primers and Phi29 DNA polymerase based rolling circle amplification as described. Ct values were determined for each sample in a serial 10x dilution series. The similar Ct values for each amount of input nucleic acid sample suggests that the beta actin transcript concentration relative to the entire sample is accurately maintained throughout the procedure.

In one embodiment, the mRNA is replicated to make a cDNA:mRNA hybrid (first strand cDNA synthesis). The cDNA strand is then ligated to form circles (monomer size), either with or without concatemers. This ligation can be stimulated by adding an oligonucleotide which is complementary to the 5' end of the primer being used for initiation of cDNA synthesis (see FIG. 5). This ligated material can then be amplified by ASD (rolling circle amplification or strand displacement amplification). The methodology permits both random primed and specific primed amplification methods.

Figure 2:
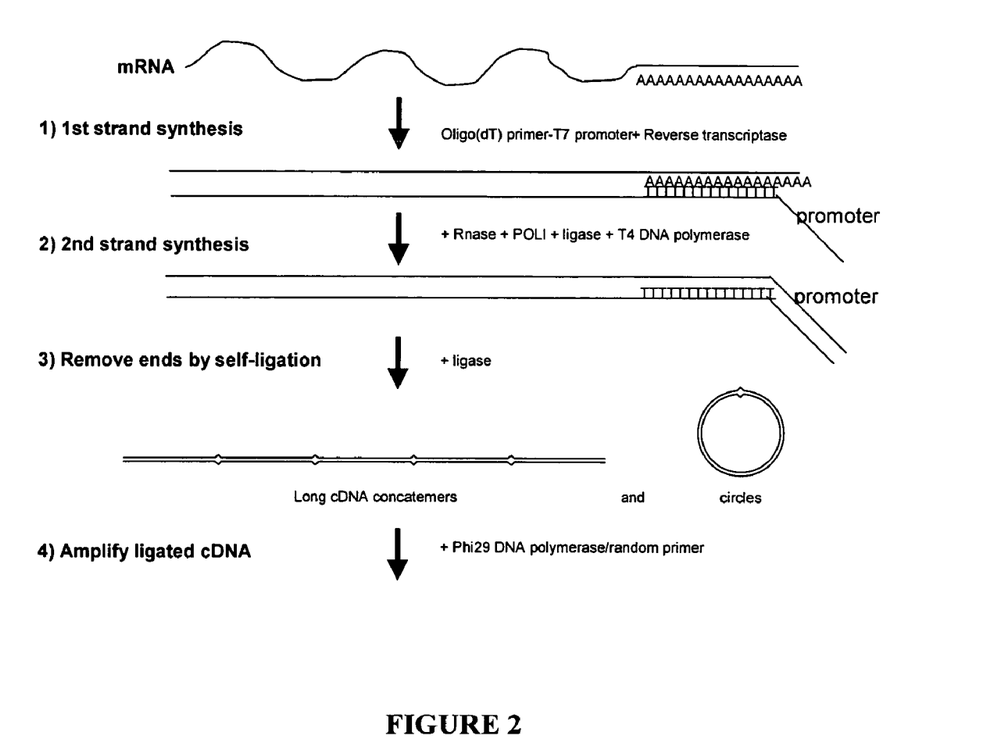
FIG. 2 presents a schematic of the amplification methodology wherein a promoter is included.

Further, unlike prior methodology, in this method the promoter-tagged cDNA is used as a template for cDNA ligation, ligating to form either circles or concatemers or a mixture of both, which are then amplified by rolling circle amplification or strand displacement amplification (see FIG. 2). The amplified material can then be transcribed for use in quantification studies, thereby providing greater amplification than what is currently available. Additionally, if the oligonucleotide used to initiate first strand cDNA synthesis is promoter tagged, the resulting RNA would be antisense, which is advantageous in certain applications.

The primer used to make promoter-tagged cDNA or untagged cDNA can be designed with complementarity to the polyA tail (to anneal the polyA tail) of the RNA or to specific sequences within the RNA population. It can also be used to initiate first or second strand cDNA synthesis.

Figure 3:
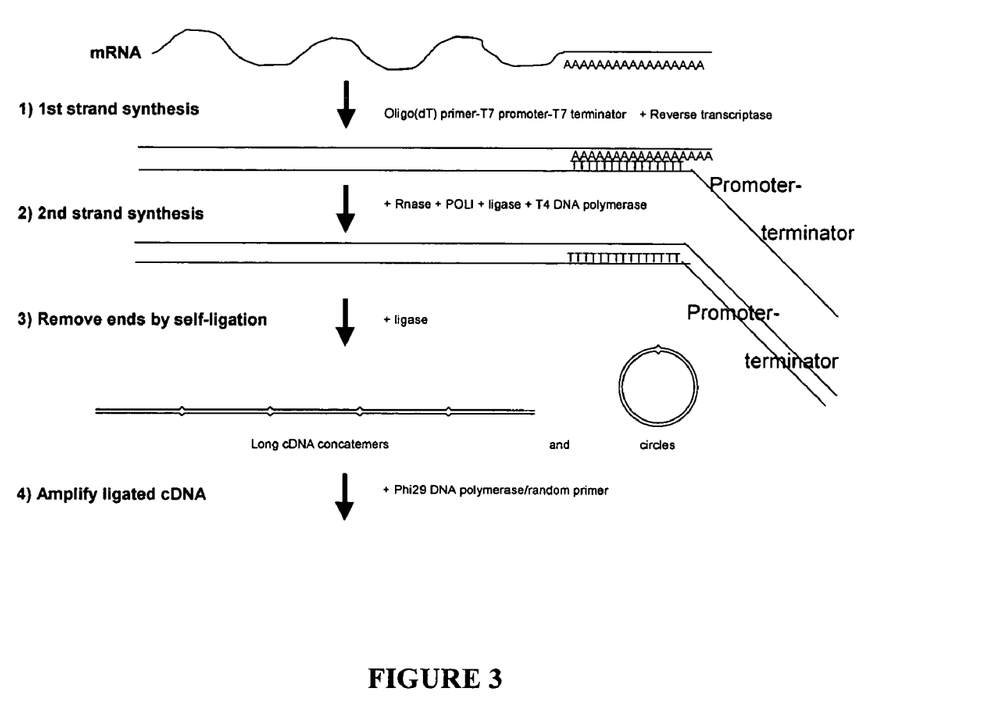
FIG. 3 presents a schematic of the methodology including a promoter/terminator sequence.
Figure 4:
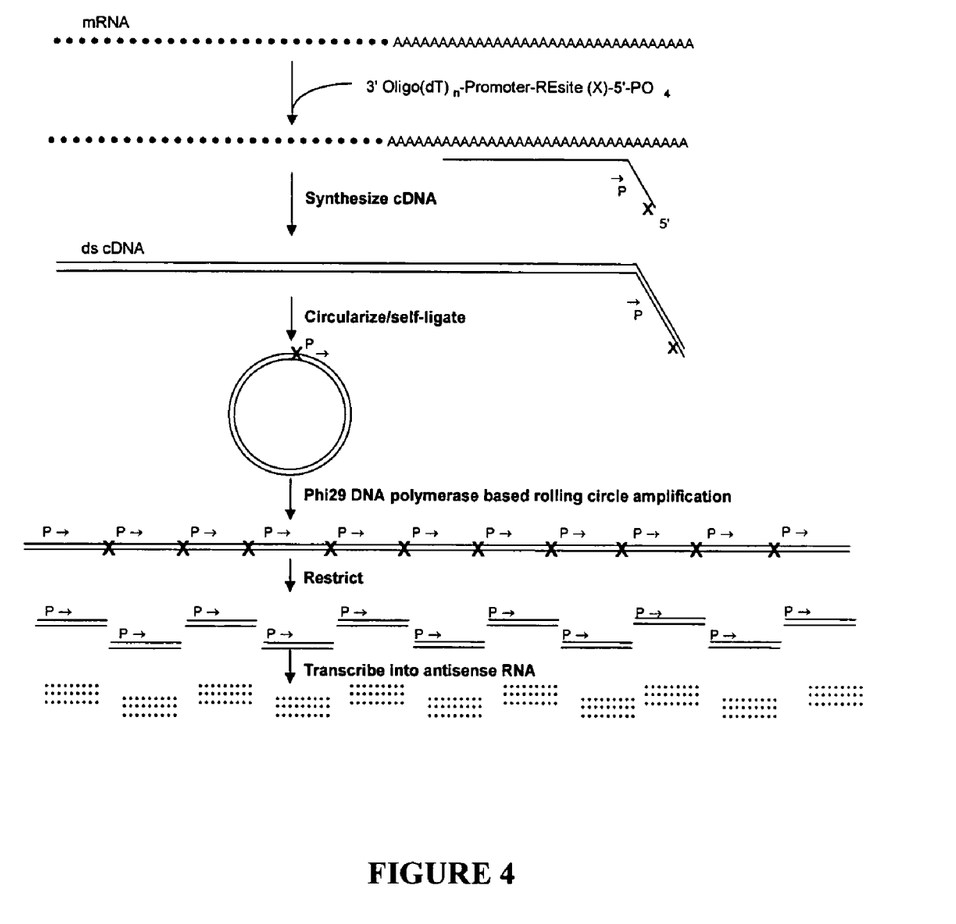
FIG. 4 presents a schematic of the methodology including a promoter/restriction enzyme recognition sequence.

Further, the strand displacement amplification of circularized or concatenated cDNA will generate end-to-end concatemers of the input template cDNA units. These units will each have a separate RNA polymerase promoter. In order to prevent overlapping transcription from these concatenated units, an RNA polymerase terminator sequence or alternatively a restriction enzyme recognition sequence can be included upstream of the promoter sequence used in the primer for first strand cDNA synthesis (see FIGS. 3 and 4). This terminator will prevent over-amplification of cDNA's resulting from repeated transcription by read-through transcription from upstream promoters.

In another preferred form of the method, referred to as strand displacement amplification of concatenated cDNA (MSDA-CD), fragments of cDNA are first concatenated together or circularized, potentially with linkers. The concatenated or circularized DNA is then amplified by strand displacement synthesis with appropriate primers. A random set of primers can be used to randomly prime synthesis of the DNA concatemers in a manner similar to whole genome amplification. As in whole genome amplification, by choosing a sufficiently large set of primers of random or partially random sequence, the primers in the set will be collectively, and randomly, complementary to nucleic acid sequences distributed throughout concatenated DNA. If linkers are used to concatenate the DNA fragments, primers complementary to linker sequences can be used to amplify the concatemers. Synthesis proceeds from the linkers, through a section of the concatenated DNA to the next linker, and continues beyond. As the linker regions are replicated, new priming sites for DNA synthesis are created. In this way, multiple overlapping copies of the entire concatenated DNA sample can be synthesized in a short time.

A means of amplifying circular target DNA molecules is of value because such amplified DNA is frequently used in subsequent methods including DNA sequencing, cloning, mapping, genotyping, generation of probes, and diagnostic identification.

Heretofore, several useful methods were developed that permit amplification of nucleic acids. Most were designed around the amplification of selected DNA targets and/or probes, including the polymerase chain reaction (PCR), ligase chain reaction (LCR), self-sustained sequence replication (3SR), nucleic acid sequence based amplification (NASBA), strand displacement amplification (SDA), and amplification with Q.beta. replicase (Birkenmeyer and Mushahwar, J. Virological Methods, 35:117-126 (1991); Landegren, Trends Genetics, 9:199-202 (1993)).

In addition, several methods have been employed to amplify circular DNA molecules such as plasmids or DNA from bacteriophage such as M13. One has been propagation of these molecules in suitable host strains of *E. coli*, followed by isolation of the DNA by well-established protocols (Sambrook, J., Fritsch, E. F., and Maniatis, T. Molecular Cloning, A Laboratory Manual, 1989, Cold Spring Harbor Laboratory Press, Cold Spring Harbor, N.Y.). PCR has also been a frequently used method to amplify defined sequences in DNA targets such as plasmids and DNA from bacteriophage such as M13 (PCR Protocols, 1990, Ed. M. A. Innis, D. H. Gelfand, J. J. Sninsky, Academic Press, San Diego.) Some of these methods suffer from being laborious, expensive, time-consuming, inefficient, and lacking in sensitivity.

As an improvement on these methods, linear rolling circle amplification (LRCA) uses a primer annealed to a circular target DNA molecule and DNA polymerase is added. The amplification target circle (ATC) forms a template on which new DNA is made, thereby extending the primer sequence as a continuous sequence of repeated sequences complementary to the circle but generating only about several thousand copies per hour. An improvement on LRCA is the use of exponential RCA (ERCA), with additional primers that anneal to the replicated complementary sequences to provide new centers of amplification, thereby providing exponential kinetics and increased amplification.

Exponential rolling circle amplification (ERCA) employs a cascade of strand displacement reactions, also referred to as HRCA (Lizardi, P. M. et al. Nature Genetics, 19, 225-231 (1998)). However, ERCA is limited to the use of just a single primer P1 annealed to the circular DNA target molecule, to the need to know the specific DNA sequence for the primer P1, and for the need of the circular DNA target molecule to be a single-stranded DNA circle.

The methods of the present invention (referred to herein as Multiply-Primed Rolling Circle Amplification—MPRCA) avoid such disadvantages by employing procedures that improve on the sensitivity of linear rolling circle amplification by using multiple primers for the amplification of individual target circles. The present invention has the advantage of generating multiple tandem-sequence DNA (TS-DNA) copies from each circular target DNA molecule. In addition, MPRCA has the advantages that in some embodiments the sequence of the circular target DNA molecule may be unknown while the circular target DNA molecule may be single-stranded (ssDNA) or double-stranded (dsDNA or duplex DNA). Another advantage of some embodiments of the present invention is that the amplification of single-stranded or double-stranded circular target DNA molecules may be carried out isothermally and/or at ambient temperatures. Other advantages include being highly useful in new applications of rolling circle amplification, low cost, sensitivity to low concentration of target circle, flexibility, especially in the use of detection reagents, and low risk of contamination.

In some embodiments of the present invention, procedures are employed that improve on the yield of amplified product DNA by using primers that are resistant to degradation by exonuclease activity that may be present in the reaction. For example, a primer may possess one, two, three or four phosphorothioate linkages between nucleotides at the 3' end of the primer. Thus, in some embodiments, the present invention relates to processes wherein the primers contain at least one nucleotide that makes the primer resistant to degradation, commonly by an enzyme, especially by an exonuclease and most especially by 3'-5'-exonuclease activity. In such an embodiment, at least one nucleotide may be a phosphorothioate nucleotide or some modified nucleotide. Such nucleotide is commonly a 3'-terminal nucleotide but the processes of the present invention also relate to embodiments wherein such a nucleotide is located at other than the 3'-terminal position and wherein the 3'-terminal nucleotide of said primer can be removed by 3'-5'-exonuclease activity. This has the advantage of permitting the primers to persist in reactions that contain an exonuclease activity and that may be carried out for long incubation periods. The persistence of the primers allows new priming events to occur for the entire incubation time of the reaction, which is one of the hallmarks of ERCA and has the advantage of increasing the yield of amplified DNA.

Random primer RCA also has the benefit of generating double stranded products. This is because the linear ssDNA products generated by copying of the circular template will themselves be converted to duplex form by random priming of DNA synthesis. Double stranded DNA product is advantageous in allowing for DNA sequencing of either strand and for restriction endonuclease digestion and other methods used in cloning, labeling, and detection. Double stranded DNA product is also advantageous in allowing for in vitro transcription using RNA polymerase.

It is also expected that strand-displacement DNA synthesis may occur during random priming RCA resulting in an exponential amplification.

Following amplification, the amplified sequences can be for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. DNA that has been produced using the disclosed method can then be used for any purpose or in any other method desired. For example, PCR can be used to further amplify any specific DNA sequence that has been previously amplified by the whole genome strand displacement method.

The objects and features of the invention are more fully apparent following review of the detailed description of the invention in conjunction with the accompanying drawings.

BRIEF DESCRIPTION OF THE DRAWINGS

FIG. 6 presents the results from microarray analysis comparison of amplified cDNA and direct $1^{st}$ strand cDNA labeling. Comparison of expression levels using signal strengths obtained using labeled material from Skeletal Muscle tissue with a CyScribe first strand cDNA kit (Amersham Biosciences) or labeled material obtained after cDNA synthesis, circularization, amplification, restriction digest and in vitro transcription (as described). The plot shows the normalized signal ratios for 600 spots. These data indicate that gene expression information is accurately maintained using the described amplification procedure.

DETAILED DESCRIPTION OF INVENTION

The disclosed method makes use of certain 1) materials and 2) procedures, which allow amplification of target nucleic acid sequences and whole genomes or other highly complex nucleic acid samples. These materials and procedures are described in detail below.

1. Materials

Target Sequence

The target sequence, which is the object of amplification in the present method, is circularized or concatenated cDNA. The nucleic acid sample comprising the target sequence, can be a nucleic acid sample from a single cell.

Address Tag

Another example of a sequence that can be included in the non-complementary portion of a primer is an address tag. An address tag has a sequence complementary to an address probe. Address tags become incorporated at the ends of amplified strands. The result is amplified DNA having address tag sequences that are complementary to the complementary portion of address probes. If present, there may be one, or more than one, address tag on a primer. It is preferred that a primer have one or two address tags. Most preferably, a primer will have one address tag. Generally, it is preferred that a primer have 10 address tags or less. There is no fundamental limit to the number of address tags that can be present on a primer except the size of the primer. When there are multiple address tags, they may have the same sequence or they may have different sequences, with each different sequence complementary to a different address probe. It is preferred that a primer contain address tags that have the same sequence such that they are all complementary to a single address probe. The address tag portion can be any length that supports specific and stable hybridization between the address tag and the address probe. For this purpose, a length between 10 and 35 nucleotides long is preferred, with an address tag portion 15 to 20 nucleotides long being most preferred.

Linkers

As used herein for concatenating DNA, a linker is a small, double-stranded DNA molecule. For SDA-CD, linkers serve two main purposes; facilitating concatenation of DNA fragments and facilitating amplification. For the first purpose, linkers are generally designed to have ends compatible with the ends of the DNA fragments to be concatenated. For example, if the DNA fragments have blunt ends (or the ends will be made blunt), blunt ended linkers would be used. For DNA fragments that have been tailed with one or more nucleotides, the linkers should have a complementary tail. An example of such tailing is the addition of single adenosine residues to the 3' ends of cDNA. For facilitating amplification, linkers should have one or more sequences complementary to primers to be used in MSDA-CD. Such sequences are referred to as primer complement portions of the linkers. Primer complement portions of linkers are complementary to complementary portions of primers. A primer complement portion can have an arbitrary sequence so long as it is complementary to the portion of the intended primer. If there are primer complement portions on opposite strands of the linker, they should not overlap. The primer can also have one or more restriction enzyme cleavage sites. Such restriction sites allow the amplified DNA to be cut into fragments, and preferably into fragments representing the original DNA fragments which were concatenated. For this purpose, it is preferred that a rare restriction site be used (for example, an eight-base recognition site). An example of the structure of a linker of this type is illustrated below.

```
          Primer >        Restriction Site
P-NNNNNNNNNNNNNNNNNNNNNNNNNNNNNNNNNNNNNNNNNNNNNNNNNNT TNNNNNNNNNNNNNNNNNNNNNNNNNNNNNNNNNNNNNNNNNNNNNNNNNNN-P
                                              <Primer 2
```

Linkers can also contain one or more promoter sequences. Such promoter sequences allow the amplified DNA to be further amplified by transcription after MSDA-CD. If two promoters are incorporated into the linker, they are preferably located on different strands of the linker. An example of a linker, having a single protruding thymidine residue at both 3' termini, and a phosphate group at both 5' termini, is illustrated below (P indicates phosphate).

```
       Primer 1>          Promoter 1>
P-NNNNNNNNNNNNNNNNNNNNNNNNNNNNNNNNNNNNNNNNNNNNNNNNNNT TNNNNNNNNNNNNNNNNNNNNNNNNNNNNNNNNNNNNNNNNNNNNNNNNNNN-P
           <Promoter 2              <Primer 2
```

The promoter and primer sequences may be arranged in any order, but the arrangement shown above is preferred. Any number of primers and promoters may be used. However, it is preferred that, where the DNA to be concatenated is cDNA, promoters be incorporated into the cDNA as part of the primers used for cDNA synthesis (Lockhart et al.).

Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are a preferred form of detection label since they can be directly incorporated into the amplification products during synthesis. Examples of detection labels that can be incorporated into amplified DNA or RNA include nucleotide analogs such as BrdUrd (Hoy and Schimke, Mutation Research 290:217-230 (1993)), BrUTP (Wansick et al., J. Cell Biology 122:283-293 (1993)) and nucleotides modified with biotin (Langer et al., Proc. Natl. Acad. Sci. USA 78:6633 (1981)) or with suitable haptens such as digoxygenin (Kerkhof, Anal. Biochem. 205:359-364 (1992)). Suitable fluorescence-labeled nucleotides are Fluorescein-isothiocyanate-dUTP, Cyanine-3-dUTP and Cyanine-5-dUTP (Yu et al., Nucleic Acids Res., 22:3226-3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringher Mannheim). Fluorescein, Cy3, and Cy5 can be linked to dUTP for direct labelling. Cy3.5 and Cy7 are available as avidin or anti-digoxygenin conjugates for secondary detection of biotin- or digoxygenin-labelled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,dioxetane-3-2'-(5'-chloro)tricyclo [3.3.1.1.sup.3,7]decane]-4-yl) phenyl phosphate; Tropix, Inc.).

A preferred detection label for use in detection of amplified RNA is acridinium-ester-labeled DNA probe (GenProbe, Inc., as described by Arnold et al., Clinical Chemistry 35:1588-1594 (1989)). An acridinium-ester-labeled detection probe permits the detection of amplified RNA without washing because unhybridized probe can be destroyed with alkali (Arnold et al. (1989)).

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

Detection Probes

Detection probes are labeled oligonucleotides having sequence complementary to detection tags on amplified nucleic acids. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, Nature Biotechnol. 14:303-309 (1995)). The use of such probes eliminates the need for removal of unhybridized probes prior to label detection because the unhybridized detection probes will not produce a signal. This is especially useful in multiplex assays.

Address Probes

An address probe is an oligonucleotide having a sequence complementary to address tags on primers. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. An address probe can contain a single complementary portion or multiple complementary portions. Preferably, address probes are coupled, either directly or via a spacer molecule, to a solid-state support. Such a combination of address probe and solid-state support are a preferred form of solid-state detector.

Oligonucleotides

Primers, detection probes, address probes, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, Biochemistry 34:10807-10815 (1995), McGraw et al., Biotechniques 8:674-678 (1990), and Rychlik et al., Nucleic Acids Res. 18:6409-6412 (1990).

Solid-State Detectors

Solid-state detectors are solid-state substrates or supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a microtiter dish. The most preferred form of microtiter dish is the standard 96-well type.

Address probes immobilized on a solid-state substrate allow capture of the products of the disclosed amplification method on a solid-state detector. Such capture provides a convenient means of washing away reaction components that might interfere with subsequent detection steps. By attaching different address probes to different regions of a solid-state detector, different amplification products can be captured at different, and therefore diagnostic, locations on the solid-state detector. For example, in a microtiter plate multiplex assay, address probes specific for up to 96 different amplified nucleic acids (each representing a different target sequence amplified via a different set of primers) can be immobilized on a microtiter plate, each in a different well. Capture and detection will occur only in those wells corresponding to amplified nucleic acids for which the corresponding target sequences were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., Proc. Natl. Acad. Sci. USA 91(11):5022-5026 (1994), and Khrapko et al., Mol Biol (Mosk) (USSR) 25:718-730 (1991). A method for immobilization of 3'-amine oligonucleotides on casein-coated slides is described by Stimpson et al., Proc. Natl. Acad. Sci. USA 92:6379-6383 (1995). A preferred method of attaching oligonucleotides to solid-state substrates is described by Guo et al., Nucleic Acids Res. 22:5456-5465 (1994).

Solid-State Samples

Solid-state samples are solid-state substrates or supports to which target sequences have been coupled or adhered. Target sequences are preferably delivered in a target sample or assay sample. A preferred form of solid-state sample is an array sample. An array sample is a solid-state sample to which multiple different target sequences have been coupled or adhered in an array, grid, or other organized pattern.

Solid-state substrates for use in solid-state samples can include any solid material to which target sequences can be coupled or adhered. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, slides, fibers, woven fibers, shaped polymers, particles and microparticles. Preferred forms for a solid-state substrate are microtiter dishes and glass slides. The most preferred form of microtiter dish is the standard 96-well type.

Target sequences immobilized on a solid-state substrate allow formation of target-specific amplified nucleic acid localized on the solid-state substrate. Such localization provides a convenient means of washing away reaction components that might interfere with subsequent detection steps, and a convenient way of assaying multiple different samples simultaneously. Amplified nucleic acid can be independently formed at each site where a different sample is adhered. For immobilization of target sequences or other oligonucleotide molecules to form a solid-state sample, the methods described above for can be used.

A preferred form of solid-state substrate is a glass slide to which up to 256 separate target samples have been adhered as an array of small dots. Each dot is preferably from 0.1 to 2.5 mm in diameter, and most preferably around 2.5 mm in diameter. Such microarrays can be fabricated, for example, using the method described by Schena et al., Science 270: 487-470 (1995). Briefly, microarrays can be fabricated on poly-L-lysine-coated microscope slides (Sigma) with an arraying machine fitted with one printing tip. The tip is loaded with 1 .mu.l of a DNA sample (0.5 mg/ml) from, for example, 96-well microtiter plates and deposited .about.0.005 .mu.l per slide on multiple slides at the desired spacing. The printed slides can then be rehydrated for 2 hours in a humid chamber, snap-dried at 100. degree. C. for 1 minute, rinsed in 0.1% SDS, and treated with 0.05% succinic anhydride prepared in buffer consisting of 50% 1-methyl-2-pyrrolidinone and 50% boric acid. The DNA on the slides can then be denatured in, for example, distilled water for 2 minutes at 90.degree. C. immediately before use. Microarray solid-state samples can scanned with, for example, a laser fluorescent scanner with a computer-controlled XY stage and a microscope objective. A mixed gas, multiline laser allows sequential excitation of multiple fluorophores.

DNA Polymerases

DNA polymerases useful in the multiple displacement amplification must be capable of displacing, either alone or in combination with a compatible strand displacement factor, a hybridized strand encountered during replication. Such polymerases are referred to herein as strand displacement DNA polymerases. It is preferred that a strand displacement DNA polymerase lack a 5' to 3' exonuclease activity. Strand displacement is necessary to result in synthesis of multiple copies of a target sequence. A 5' to 3' exonuclease activity, if present, might result in the destruction of a synthesized strand. It is also preferred that DNA polymerases for use in the disclosed method are highly processive. The suitability of a DNA polymerase for use in the disclosed method can be readily determined by assessing its ability to carry out strand displacement replication. Preferred strand displacement DNA polymerases are Bst large fragment DNA polymerase (Exo(-) Bst; Aliotta et al., Genet. Anal. (Netherlands) 12:185-195 (1996)) and exo(-)Bca DNA polymerase (Walker and Linn, Clinical Chemistry 42:1604-1608 (1996)). Other useful polymerases include bacteriophage .phi.29 DNA polymerase (U.S. Pat. Nos. 5,198,543 and 5,001,050 to Blanco et al.), phage M2 DNA polymerase (Matsumoto et al., Gene 84:247 (1989)), phage .phi.PRD1 DNA polymerase (Jung et al., Proc. Natl. Acad. Sci. USA 84:8287 (1987)), exo(-)VENT.RTM. DNA polymerase (Kong et al., J. Biol. Chem. 268:1965-1975 (1993)), Klenow fragment of DNA polymerase I (Jacobsen et al., Eur. J. Biochem. 45:623-627 (1974)), T5 DNA polymerase (Chatterjee et al., Gene 97:13-19 (1991)), Sequenase (U.S. Biochemicals), PRD1 DNA polymerase (Zhu and Ito, Biochim. Biophys. Acta. 1219:267-276 (1994)), and T4 DNA polymerase holoenzyme (Kaboord and Benkovic, Curr. Biol. 5:149-157 (1995)).

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. Strand displacement factors useful in strand displacement replication include BMRF1 polymerase accessory subunit (Tsurumi et al., J. Virology 67(12):7648-7653 (1993)), adenovirus DNA-binding protein (Zijderveld and van der Vliet, J. Virology 68(2):1158-1164 (1994)), herpes simplex viral protein ICP8 (Boehmer and Lehman, J. Virology 67(2):711-715 (1993); Skaliter and Lehman, Proc. Natl. Acad. Sci. USA 91(22):10665-10669 (1994)); single-stranded DNA binding proteins (SSB; Rigler and Romano, J. Biol. Chem. 270:8910-8919 (1995)); phage T4 gene 32 protein (Villemain and Giedroc, Biochemistry 35:14395-14404 (1996); and calfthymus helicase (Siegel et al., J. Biol. Chem. 267: 13629-13635 (1992)).

The ability of a polymerase to carry out strand displacement replication can be determined by using the polymerase in a strand displacement replication assay. Such assays should be performed at a temperature suitable for optimal activity for the enzyme being used, for example, 32.degree. C. for .phi.29 DNA polymerase, from 46.degree. C. to 64.degree. C. for exo(-) Bst DNA polymerase, or from about 60.degree. C. to 70.degree. C. for an enzyme from a hyperthermophylic organism. For assays from 60.degree. C. to 70.degree. C., primer length may be increased to 20 bases for random primers, or to 22 bases for specific primers. Another useful assay for selecting a polymerase is the primer-block assay described in Kong et al., J. Biol. Chem. 268:1965-1975 (1993). The assay consists of a primer extension assay using an M13 ssDNA template in the presence or absence of an oligonucleotide that is hybridized upstream of the extending primer to block its progress. Enzymes able to displace the blocking primer in this assay are useful for the disclosed method.

The materials described above can be packaged together in any suitable combination as a kit useful for performing the disclosed method.

2. Procedures

The disclosed method is based on strand displacement replication of the nucleic acid sequences by multiple primers. The method can be used to amplify one or more specific sequences (strand displacement amplification) or other cDNA of high complexity, or concatenated or circularized cDNA. The method generally involves hybridization of primers to a target nucleic acid sequence and replication of the target sequence primed by the hybridized primers such that replication of the target sequence results in replicated strands complementary to the target sequence. During replication, the growing replicated strands displace other replicated strands from the target sequence (or from another replicated strand) via strand displacement replication. Examples of such displacement of replicated strands are illustrated in U.S. Pat. No. 6,323,009. As used herein, a replicated strand is a nucleic acid strand resulting from elongation of a primer hybridized to a target sequence or to another replicated strand. Strand displacement replication refers to DNA replication where a growing end of a replicated strand encounters and displaces another strand from the template strand (or from another replicated strand). Displacement of replicated strands by other replicated strands is a hallmark of the disclosed method which allows multiple copies of a target sequence to be made in a single, isothermal reaction.

Following amplification, the amplified sequences can be used for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. Additionally, amplified sequences can be used to make materials suitable for gene expression analysis. This includes microarray analysis and other quantitative methods used to perform gene expression analysis. Amplification products can also be used to examine alternatively spliced transcripts, edited RNA sequence and for gene cloning experiments.

It is preferred that the set of primers used for SDA have a sequence composition and be used at concentrations that allow the primers to hybridize at desired intervals within the nucleic acid sample. For example, by using a set of primers at a concentration that allows them to hybridize, on average, every 4000 to 8000 bases, DNA replication initiated at these sites will extend to and displace strands being replicated from adjacent sites. It should be noted that the primers are not expected to hybridize to the target sequence at regular intervals. Rather, the average interval will be a general function of primer concentration.

As in strand displacement amplification, displacement of an adjacent strand makes it available for hybridization to another primer and subsequent initiation of another round of replication. The interval at which primers in the set of primers hybridize to the target sequence determines the level of amplification. For example, if the average interval is short, adjacent strands will be displaced quickly and frequently. If the average interval is long, adjacent strands will be displaced only after long runs of replication.

In the disclosed method, the DNA polymerase catalyzes primer extension and strand displacement in a processive strand displacement polymerization reaction that proceeds as long as desired, generating molecules of up to 60,000 nucleotides or larger. Preferred strand displacing DNA polymerases are large fragment Bst DNA polymerase (Exo(−) Bst), exo(−)Bca DNA polymerase, the DNA polymerase of the bacteriophage .phi.29 and Sequenase. During strand displacement replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al. (1981)).

Strand Displacement Amplification of Concatenated DNA

In another preferred form of the method, referred to as strand displacement amplification of concatenated DNA (MSDA-CD), concatenated DNA is amplified. A preferred form of concatenated DNA is concatenated cDNA. Concatenated DNA can be amplified using a random or partially random set of primers, as in whole genome strand displacement amplification (WGSDA), or using specific primers complementary to specific hybridization targets in the concatenated DNA. MSDA-CD is preferred for amplification of a complex mixture or sample of relatively short nucleic acid samples (that is, fragments generally in the range of 100 to 6,000 nucleotides). Messenger RNA is the most important example of such a complex mixture. MSDA-CD provides a means for amplifying all cDNAs in a cell is equal fashion. Because the concatenated cDNA can be amplified over 100-fold, MSDA-CD will permit RNA profiling analysis based on just a few cells. To perform MSDA-CD, DNA must first be subjected to a concatenation step. If an RNA sample (such as mRNA) is to be amplified, the RNA is first converted to a double-stranded cDNA using standard methods. The cDNA, or any other set of DNA fragments to be amplified, is then converted into a DNA concatenate, potentially with incorporation of linkers.

DNA fragments can be concatenated by ligation using standard conditions. The state of the ends of the DNA fragments, such as blunt, staggered or ragged, should be taken into account when concatenating DNA. For example, staggered ends, such as those produced by digestion with restriction enzymes, can be used to mediate concatenation if the overhanging sequences are compatible. DNA with ragged or staggered ends can be made blunt ended prior to ligation. All of these operations are well known and of general use. If linkers are used, the linkers can either be ligated to blunt ended DNA (using blunt ended linkers), or to DNA having compatible overhanging ends, in which case the linkers can be in the form of adaptors.

DNA polymerases useful in the rolling circle replication step of RCA must perform rolling circle replication of primed single-stranded circles (or each strand of a duplex substrate). Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the amplification target circle (ATC). A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases, all of which have 3',5'-exonuclease activity, are bacteriophage .phi.29 DNA polymerase (U.S. Pat. Nos. 5,198,543 and 5,001,050 to Blanco et al.), phage M2 DNA polymerase (Matsumoto et al., Gene 84:247 (1989)), phage PRD1 DNA polymerase (Jung et al., Proc. Natl. Aced. Sci. USA 84:8287 (1987), and Zhu and Ito, Biochim. Biophys. Acta. 1219: 267-276 (1994)), VENT.TM. DNA polymerase (Kong et al., J. Biol. Chem. 268:1965-1975 (1993)), Klenow fragment of DNA polymerase I (Jacobsen et al., Eur. J. Biochem. 45:623-627 (1974)), T5 DNA polymerase (Chatterjee et al., Gene 97:13-19 (1991)), and T4 DNA polymerase holoenzyme (Kaboord and Benkovic, Curr. Biol. 5:149-157 (1995)) .phi.29 DNA polymerase is most preferred. Equally preferred polymerases include T7 native polymerase, *Bacillus stearothermophilus* (*Bst*) DNA polymerase, *Thermoanaerobacter thermohydrosulfuricus* (*Tts*) DNA polymerase (U.S. Pat. No. 5,744,312), and the DNA polymerases of *Thermus aquaticus, Thermus flavus* or *Thermus thermophilus*. Equally preferred are the .phi.29-type DNA polymerases, which are chosen from the DNA polymerases of phages: .phi.29, Cp-1, PRD1, .phi.15, .phi.21, PZE, PZA, Nf, M2Y, B103, SF5, GA-1, Cp-5, Cp-7, PR4, PR5, PR722, and L17. In a specific embodiment, the DNA polymerase is bacteriophage .phi.29 DNA polymerase wherein the multiple primers are resistant to exonuclease activity and the target DNA is linear DNA, especially high molecular weight and/or complex linear cDNA.

Strand displacement during RCA, especially where duplex ATCs are utilized as templates, can be facilitated through the use of a strand displacement factor, such as a helicase. In general, any DNA polymerase that can perform rolling circle replication in the presence of a strand displacement factor is suitable for use in the processes of the present invention, even if the DNA polymerase does not perform rolling circle replication in the absence of such a factor. Strand displacement factors useful in RCA include BMRF1 polymerase accessory subunit (Tsurumi et al., J. Virology 67(12):7648-7653 (1993)), adenovirus DNA-binding protein (Zijderveld and van der Vliet, J. Virology 68(2):1158-1164 (1994)), herpes simplex viral protein ICP8 (Boehmer and Lehman, J. Virology 67(2):711-715 (1993); Skaliter and Lehman, Proc. Natl, Acad. Sci. USA 91(22):10665-10669 (1994)), single-stranded DNA binding proteins (SSB; Rigler and Romano, J. Biol. Chem. 270:8910-8919 (1995)), and calf thymus helicase (Siegel et al., J. BioL Chem. 267:13629-13635 (1992)).

The ability of a polymerase to carry out rolling circle replication can be determined by testing the polymerase in a rolling circle replication assay such as those described in Fire and Xu, Proc. Natl. Acad. Sci. USA 92:4641-4645 (1995) and in Lizardi (U.S. Pat. No. 5,854,033, e.g., Example 1 therein).

3. Modifications and Additional Operations

Detection of Amplification Products

Amplification products can be detected directly by, for example, primary labeling or secondary labeling, as described below.

A. Primary Labeling

Primary labeling consists of incorporating labeled moieties, such as fluorescent nucleotides, biotinylated nucleotides, digoxygenin-containing nucleotides, or bromodeoxyuridine, during strand displacement replication. For example, one may incorporate cyanine dye UTP analogs (Yu et al. (1994)) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

B. Secondary Labeling with Detection Probes

Secondary labeling consists of using suitable molecular probes, referred to as detection probes, to detect the amplified DNA or RNA. For example, a primer may be designed to contain, in its non-complementary portion, a known arbitrary sequence, referred to as a detection tag. A secondary hybridization step can be used to bind detection probes to these detection tags. The detection probes may be labeled as described above with, for example, an enzyme, fluorescent moieties, or radioactive isotopes. By using three detection tags per primer, and four fluorescent moieties per each detection probe, one may obtain a total of twelve fluorescent signals for every replicated strand.

C. Multiplexing and Hybridization Array Detection

Detection of amplified nucleic acids can be multiplexed by using sets of different primers, each set designed for amplifying different target sequences. Only those primers that are able to find their targets will give rise to amplified products. There are two alternatives for capturing a given amplified nucleic acid to a fixed position in a solid-state detector. One is to include within the non-complementary portion of the primers a unique address tag sequence for each unique set of primers. Nucleic acid amplified using a given set of primers will then contain sequences corresponding to a specific address tag sequence. A second and preferred alternative is to use a sequence present in the target sequence as an address tag.

D. Enzyme-linked Detection

Amplified nucleic acid labeled by incorporation of labeled nucleotides can be detected with established enzyme-linked detection systems. For example, amplified nucleic acid labeled by incorporation of biotin-16-UTP (Boehringher Mannheim) can be detected as follows. The nucleic acid is immobilized on a solid glass surface by hybridization with a complementary DNA oligonucleotide (address probe) complementary to the target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

Linear Strand Displacement Amplification

A modified form of strand displacement amplification can be performed which results in linear amplification of a target sequence. This modified method is referred to as linear strand displacement amplification (LSDA) and is accomplished by using a set of primers where all of the primers are complementary to the same strand of the target sequence. In LSDA, as in MSDA, the set of primers hybridize to the target sequence and strand displacement amplification takes place. However, only one of the strands of the target sequence is replicated. LSDA requires thermal cycling between each round of replication to allow a new set of primers to hybridize to the target sequence. Such thermal cycling is similar to that used in PCR. Unlike linear, or single primer, PCR, however, each round of replication in LSDA results in multiple copies of the target sequence. One copy is made for each primer used. Thus, if 20 primers are used in LSDA, 20 copies of the target sequence will be made in each cycle of replication.

DNA amplified using MSDA and WGSDA can be further amplified by transcription. For this purpose, promoter sequences can be included in the non-complementary portion of primers used for strand displacement amplification, or in linker sequences used to concatenate DNA for MSDA-CD.

The invention is further described by reference to the examples below.

EXAMPLES

The following examples illustrate certain preferred embodiments of the instant invention but are not intended to be illustrative of all embodiments. These examples should not be construed as limiting the appended claims and/or the scope of this invention.

Amplification of cDNA Using Phi29 DNA Polymerase

Protocol

Part 1—ds cDNA Synthesis
1. Using total RNA samples (100ng-10 µg), generate double stranded cDNA following Timesaver cDNA synthesis kit protocol (Amersham Biosciences). Be sure to use 5' phosphorylated NotI/P-T7/oligo(dT)$_{24}$ primer. (sequence 5' phosphateGCGGCCGCGTAATACGACTCACTATAGGGTTTTTTTTTTTTTTTTTTTTTTTT3') (SEQ ID NO: 1)
2. To prepare samples for Phi29 DNA polymerase based amplification the cDNA is purified by ethanol precipitation (add $\frac{1}{10}^{th}$ volume 1.5 M NaOAc/250 mM EDTA and 3 volumes of 100% ETOH. Centrifuge 30 minute in a microfuge.).
3. Resuspend in 10 µl of dH$_2$O.
4. The recovery of cDNA can be determined if desired (picogreen or agarose gel electrophoresis, this is optional).

Part II —Ligation
1. The ds cDNA ends are ligated to form circles.

| Components | 1 rx |
|---|---|
| cDNA (<1 µg) | 7 µl |
| 10X ligase buffer | 1 µl |
| 50% PEG-8000 | 1 µl |
| 400 units T4 DNA ligase | 1 µl |
| Total | 10 µl |

2. Incubate at 16° C. overnight.
3. Remove the samples and store at −20° C. or −80° C.

Part III —cDNA Amplification
1. Precipitate the ligated sample (add $\frac{1}{10}^{th}$ volume 1.5 M NaOAc/250 mM EDTA and 3 volumes of 100% ETOH. Centrifuge 30 minute in a microfuge.). Standard 20 µl reaction was set up as follows:

| Components | 1 rx |
|---|---|
| Ligated cDNA pellet (<1 µg) | 0 µl |
| Sample buffer (contains random primer) | 10 µl |
| Total | 10 µl |

2. Denature at 95° C. for 3 minutes.
3. Snap cool on ice.
4. Prepare a master mix combining 9 µl Reaction buffer (contains nucleotides and buffer) and 1 µl Phi29 DNA polymerase/random primer mix in a separate tube and store on ice.
5. Add 10 µl of above master mix (Reaction buffer+Enzyme) to the denatured sample.
6. Mix gently and centrifuge briefly.
7. Total reaction volume is 20 µl.
8. Incubate at 30° C. for 12-16 hrs to perform cDNA amplification.
9. Incubate sample at 65° C. for 10 minutes to inactivate the Phi29 DNA polymerase
10. Add 100 units NotI (New England Biolabs), incubate for 1 hour at 37° C.
11. Quantification of amplification product using picogreen assay or gel electrophoresis.

Part IV—In Vitro Transcription to Make Labeled Antisense RNA
1. Labeled RNA probes are generated (using amplified, restriction digested DNA) to hybridize on Micro array slides.
   Note: protect from direct light exposure. Care should be taken to avoid RNase contamination.
2. Multiple reaction can be set for each dye with each template. Use MAXIscript in vitro transcription kit (Ambion).

| Components | 1RX | 4.5RX | Final Conc. |
|---|---|---|---|
| DNA Template* | 5 | 22.5 | 1 µg |
| 10X Transcription buffer | 2 | 9 | 1X |
| 10 mM rATP | 1 | 4.5 | 50 µM |
| 10 mM rCTP | 1 | 4.5 | 50 µM |
| 10 mM rGTP | 1 | 4.5 | 50 µM |
| 10 mM rUTP | 0.6 | 2.7 | 50 µM |
| Cy3 rUTP or Cy5 rUTP (Amersham Biosciences) | 0.4 | 1.8 | 50 µM |
| RNase inhibitor | 1 | 4.5 | 20 U |
| T7 RNA pol mix | 2 | 9 | 30 U |
| DEPC dH$_2$O | 6 | 27 | |
| Total | 20 | 90 | |

3. Incubate at 37° C. for 2-4 hrs.
4. Stop reaction by adding 1 µl of 0.5 M EDTA.
   *DNA Sample volume change for each set of reaction along with DEPC dH$_2$O to final volume of 20 µl Part VI—Purification Purification Using RNeasy Mini Kit (Qiagen)
1. Follow the protocol for RNA cleanup from the protocol booklet.
2. After wash step, samples were recovered first with 50 µl of depc dH$_2$O and second elution with 30 µl depc dH$_2$O, to a total volume of ~80 µl.
3. If for each dye multiple reactions were done, reactions can be pooled together in to one tube.
4. Quantitation with 1:5 dilution of probe by spectrophotometer reading (Cy5 O.D @650 nm, Cy3 O.D @550 nm) and running 10-15% Polyacrylamide gel Samples can be purified by ethanol precipitation if desired.

Part VII—Fragmentation of Labeled RNA (Optional)
1. 3-4 µg of labeled RNA was treated with 5× fragmentation buffer.

| 5X fragmentation buffer | |
|---|---|
| Tris base | 6.06 g |
| DEPC dH$_2$O | 175 ml |

Dissolve completely
Adjust pH to 8.1(with glacial acetic acid)
Add:

| Potassium acetate | 12.3 g |
|---|---|
| Magnesium acetate | 8.04 g |

Dissolve and adjust volume to 250 ml
Final pH ~8.4
Filter sterilize
Aliquot and store at −20° C.

| Components | 1 rx | Final Conc. |
|---|---|---|
| Probe (Labeled RNA) | X μl | 3-4 μg |
| 5X fragmentation buffer | 10 μl | 0.5 X |
| DEPC dH$_2$O | X μl | |
| Total | 100 μl | |

2. Incubate at 95° C. for 35 mins
3. Slowly cooled at RT. Place tubes on ice.
4. Proceed immediately to ethanol precipitation.
5. Add 10 μl of 5 M Ammonium acetate (DEPC)
6. Add 300 μl of 100% cold ethanol
7. Store at −80° C. for 30 mins
8. Centrifuge at high speed in refrigerated centrifuge for 20 mins.
9. Discard supernatant
10. Wash with 70% (DEPC) ethanol
11. Air dry pellet quickly.
12. Resuspended in 6 μl of DEPC dH$_2$O.
13. Fragmented probe can be stored at −80° C.

Part VIII—Hybridization on Microarray Slides
1. Manual—Preparation of hybridization Mix

| Components | 1 rx |
|---|---|
| Fragmented RNA probe | 6 μl |
| 50% formamide | 15 μl |
| 4X hybridization buffer | 7.5 μl |
| A$_{80}$ | 1.5 μl |
| Total | 10 μl |

2. Mix gently.
3. Denature probe at 95° C. for 2 mins
4. Centrifuge at high speed for 2 mins.
5. Hybridize on Corning Mirror slides or Alice reflective slides.
6. Hybridization at 42° C. for 18 hrs in oven.

Hybridization on Automated Slide Processor (ASP)
1. Preparation of Hybridization Mix

| Components | 1 rx |
|---|---|
| Fragmented RNA probe | 22.5 μl |
| 50% formamide | 115 μl |
| 4X hybridization buffer | 58 μl |
| A$_{80}$ | 11.5 μl |
| 8M Urea | 23 μl |
| Total | 10 μl |

2. Mix gently.
3. Denature probe at 95° C. for 2 mins
4. Centrifuge at high speed for 2 mins.
5. Hybridize on Coming Mirror slides or Alice reflective slides.
6. Hybridization at 42° C. for 18 hrs in oven.

| Part IX - Wash Buffers and Conditions | | | |
|---|---|---|---|
| 1. | 2X SSC/0.2% SDS | 55° C. prewarmed (to remove cover slip) | <2 mins |
| 2. | 1X SSC/0.2% SDS | RT Slide chamber | 2 mins |
| 3. | 0.1X SSC/0.2% SDS | RT Slide chamber | 2 mins |
| 4. | 0.1X SSC | dipping three times | |
| 5. | DEPC dH$_2$O | dipping once | |
| 6. | immediately slides were dried with gently flow of N$_2$ | | |
| 7. | Scan Cy3 @550 pmt/Cy5 @ 600 pmt. | | |

Part X—Quantitative Real Time PCR Analysis
1. Using Human lung mRNA sample, generated first strand cDNA, double stranded cDNA and amplified cDNA, series of 10× serial dilutions of samples were made to quantitative expression levels.
2. The MGB Eclipse™ probe system for Beta-Actin (cDNA) is used for detecting and quantifying the expression levels in the samples. DNA probe specific for Beta-actin transcripts were generated (amplicon size of 89 base pairs) using Forward primer (5'GCG TGA TGG TGG GCA T (sense)) (SEQ ID NO: 2), Reverse primer (5'GAT GG*G GTA CTT CAG GGT (antisense)) (SEQ ID NO: 3) with FAM labeled probe (5' MGB-EDQ-GGA TTC CTA TGT GGG CGA (sense)) (SEQ ID NO: 4).
3. Quantitative real time PCR set up as follows:

| Components | 1 rx |
|---|---|
| RNase free water | X μl* |
| Hybridization buffer | 2.5 μl |
| 10 mM dNTP's | 1 μl |
| 20Xprimer mix | 1.25 μl |
| 20Xprobe | 1.25 μl |
| Jump start Taq | 0.4 μl |
| Template | X μl* |
| Total | 25 μl |

Template volume changes for each set of reactios along with DEPC dH$_2$O to final volume of 25 μl
4. PCR conditions: 95° 2 mins, 50 Cycles at 95° 10 sec., 56° 30 sec., 760° 30 sec.

Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method of amplifying RNA sequences comprising:
   a) reverse transcribing of RNA to form a cDNA:RNA duplex;
   b) self-ligating said cDNA, without first removing said RNA from said duplex, to form circular cDNA products; and
   c) amplifying the ligated cDNA products by rolling circle amplification using nuclease resistant random-sequence primers and DNA polymerase.

2. The method of claim 1, wherein the DNA polymerase has strand displacement activity.

3. The method of claim 1, wherein the DNA polymerase is selected from the group consisting of *Thermoanaerobacter thermohydrosulfuricus* DNA polymerase, *Thermococcus litoralis* DNA polymerase I, *E. coli* DNA polymerase I, Taq DNA polymerase I, Tth DNA polymerase I, *Bacillus stearothermophilus* (Bst) DNA polymerase I, *E. coli* DNA polymerase III, bacteriophage T5 DNA polymerase, bacteriophage M2 DNA polymerase, bacteriophage T4 DNA polymerase, bacteriophage T7 DNA polymerase, bacteriophage phi29 DNA polymerase, bacteriophage PRD1 DNA polymerase, bacteriophage phi15 DNA polymerase, bacteriophage phi21DNA polymerase, bacteriophage PZE DNA polymerase, bacteriophage PZA DNA polymerase, bacteriophage Nf DNA polymerase, bacteriophage M2Y DNA polymerase, bacteriophage B103 DNA polymerase, bacteriophage SF5 DNA polymerase, bacteriophage GA-1 DNA polymerase, bacteriophage Cp-5 DNA polymerase, bacteriophage Cp-7 DNA polymerase, bacteriophage PR4 DNA polymerase, bacteriophage PR5 DNA polymerase, bacteriophage PR722 DNA polymerase and bacteriophage L17 DNA polymerase.

4. The method of claim 1, wherein said reverse transcribing step is performed using a second primer that comprises the sequence of an RNA polymerase promoter; which method further comprises:
   d) transcribing the resulting amplified, promoter-containing DNA using RNA polymerase.

5. The method of claim 4, wherein the RNA polymerase is T7 RNA polymerase, T3 RNA polymerase or SP6 RNA polymerase.

6. The method of claim 4, wherein said second primer further comprises a restriction enzyme recognition sequence and wherein the amplified, promoter containing DNA is treated with a restriction enzyme prior to transcribing.

7. The method of claim 4, wherein said second primer comprises an RNA polymerase termination sequence.

8. A method of amplifying RNA sequences comprising:
   a) reverse transcribing RNA to form a cDNA:RNA duplex;
   b) self-ligating the cDNA, without first removing said RNA from said duplex, to form circular cDNA products; and
   c) amplifying the resulting self-ligated cDNA by rolling circle amplification using one or more nuclease resistant specific sequence primers.

9. The method of claim 8, wherein 1 to 50 said specific sequence primers are used.

10. The method of claim 8, wherein said one or more specific sequence primers are each independently between 7 and 50 nucleotides long.

11. The method of claim 10, wherein said one or more specific sequence primers are each independently between 12 and 25 nucleotides long.

12. The method of claim 8, wherein the DNA polymerase has strand displacement activity.

13. The method of claim 8, wherein the DNA polymerase is selected from the group consisting of *Thermoanaerobacter thermohydrosulfuricus* DNA polymerase, *Thermococcus litoralis* DNA polymerase I, *E. coli* DNA polymerase I, Taq DNA polymerase I, Tth DNA polymerase I, *Bacillus stearothermophilus* (Bst) DNA polymerase I, *E. coli* DNA polymerase III, bacteriophage T5 DNA polymerase, bacteriophage M2 DNA polymerase, bacteriophage T4 DNA polymerase, bacteriophage T7 DNA polymerase, bacteriophage phi29 DNA polymerase, bacteriophage PRD1 DNA polymerase, bacteriophage phi15 DNA polymerase, bacteriophage phi21DNA polymerase, bacteriophage PZE DNA polymerase, bacteriophage PZA DNA polymerase, bacteriophage Nf DNA polymerase, bacteriophage M2Y DNA polymerase, bacteriophage B103 DNA polymerase, bacteriophage SF5 DNA polymerase, bacteriophage GA-1 DNA polymerase, bacteriophage Cp-5 DNA polymerase, bacteriophage Cp-7 DNA polymerase, bacteriophage PR4 DNA polymerase, bacteriophage PR5 DNA polymerase, bacteriophage PR722 DNA polymerase and bacteriophage L17 DNA polymerase.

14. A method of producing labeled DNA comprising, amplifying DNA according to the method of claim 1 or 8, wherein said amplifying step further comprises including one or more detectably labeled nucleotide analogs or one or more nucleotide analogs providing a means for direct or indirect attachment of a detection label.

15. A method of producing labeled RNA comprising, amplifying RNA according to the method of claim 4, wherein said transcribing step d), further comprises including one or more detectably labeled nucleotide analogs or one or more nucleotide analogs providing a means for direct or indirect attachment of a detection label.

16. A method of identifying an RNA sequence comprising, amplifying RNA according to the method of any one of claims 1, 4 or 8, and identifying the resulting amplified RNA by a sequence dependent detection method.

* * * * *